United States Patent
Villemoes et al.

(10) Patent No.: US 9,830,928 B2
(45) Date of Patent: Nov. 28, 2017

(54) OVERSAMPLING IN A COMBINED TRANSPOSER FILTERBANK

(71) Applicant: Dolby International AB, Amsterdam Zuidoost (NL)

(72) Inventors: Lars Villemoes, Järfälla (SE); Per Ekstrand, Saltsjobaden (SE)

(73) Assignee: Dolby International AB, Amsterdam (NL)

( * ) Notice: Subject to any disclaimer, the term of this patent is extended or adjusted under 35 U.S.C. 154(b) by 0 days.

(21) Appl. No.: 15/165,735

(22) Filed: May 26, 2016

(65) Prior Publication Data

US 2016/0275965 A1   Sep. 22, 2016

Related U.S. Application Data

(63) Continuation of application No. 14/505,739, filed on Oct. 3, 2014, now Pat. No. 9,384,750, which is a
(Continued)

(51) Int. Cl.
*G10L 21/038* (2013.01)
*G10L 19/26* (2013.01)
(Continued)

(52) U.S. Cl.
CPC .......... *G10L 21/038* (2013.01); *G10L 19/022* (2013.01); *G10L 19/0204* (2013.01); *G10L 19/265* (2013.01)

(58) Field of Classification Search
CPC ................................................... G10L 21/038
(Continued)

(56) References Cited

U.S. PATENT DOCUMENTS 4,016,540 A * 4/1977 Hyatt .................. B60R 16/0373
379/909
4,060,848 A * 11/1977 Hyatt .................. B60R 16/0373
705/24
(Continued)

FOREIGN PATENT DOCUMENTS

CN  1606687  4/2005
JP  3871347  10/2006
(Continued)

OTHER PUBLICATIONS

Nagel, F., et al., "A Harmonic Bandwidth Extension Method for Audio Codecs" International Conference on Acoustics, Speech and Signal Processing, Apr. 19, 2009, pp. 145-148.
(Continued)

*Primary Examiner* — Gerald Gauthier

(57) ABSTRACT

The present invention relates to coding of audio signals, and in particular to high frequency reconstruction methods including a frequency domain harmonic transposer. A system and method for generating a high frequency component of a signal from a low frequency component of the signal is described. The system comprises an analysis filter bank (501) comprising an analysis transformation unit (601) having a frequency resolution of $\Delta f$; and an analysis window (611) having a duration of $D_A$; the analysis filter bank (501) being configured to provide a set of analysis subband signals from the low frequency component of the signal; a nonlinear processing unit (502, 650) configured to determine a set of synthesis subband signals based on a portion of the set of analysis subband signals, wherein the portion of the set of analysis subband signals is phase shifted by a transposition order T; and a synthesis filter bank (504) comprising a synthesis transformation unit (602) having a frequency resolution of $Q\Delta f$; and a synthesis window (612) having a duration of $D_S$; the synthesis filter bank (504) being config-
(Continued)

ured to generate the high frequency component of the signal from the set of synthesis subband signals; wherein Q is a frequency resolution factor with Q≥1 and smaller than the transposition order T; and wherein the value of the product of the frequency resolution $\Delta f$ and the duration $D_A$ of the analysis filter bank is selected based on the frequency resolution factor Q.

20 Claims, 8 Drawing Sheets

Related U.S. Application Data continuation of application No. 13/499,893, filed as application No. PCT/EP2010/057156 on May 25, 2010, now Pat. No. 8,886,346.

(60) Provisional application No. 61/330,786, filed on May 3, 2010, provisional application No. 61/253,775, filed on Oct. 21, 2009.

(51) Int. Cl.
  *G10L 19/02* (2013.01)
  *G10L 19/022* (2013.01)

(58) Field of Classification Search
  USPC .............. 341/61; 375/241; 381/98, 17, 94.2;
  382/248, 303; 455/550.1; 700/94;
  704/200.1, 203, 207, 258, 278, 500, 503;
  708/172, 313; 712/4, 41; 600/300;
  702/76, 189
  See application file for complete search history.

(56) References Cited

U.S. PATENT DOCUMENTS

| | | | | |
|---|---|---|---|---|
| 4,395,700 | A * | 7/1983 | McCubbrey | G06K 9/56 |
| | | | | 382/205 |
| 5,235,623 | A * | 8/1993 | Sugiyama | H03M 7/3053 |
| | | | | 341/67 |
| 5,297,236 | A * | 3/1994 | Antill | G06T 9/005 |
| | | | | 704/203 |
| 5,890,106 | A * | 3/1999 | Bosi-Goldberg | H03H 17/0266 |
| | | | | 704/203 |
| 6,073,100 | A | 6/2000 | Goodridge, Jr. | |
| 6,246,345 | B1 | 6/2001 | Davidson | |
| 6,363,338 | B1 | 3/2002 | Ubale | |
| 7,483,758 | B2 | 1/2009 | Liljeryd | |
| 8,886,346 | B2 * | 11/2014 | Villemoes | G10L 21/038 |
| | | | | 381/98 |
| 9,236,061 | B2 * | 1/2016 | Ekstrand | G10L 19/022 |
| 9,384,750 | B2 * | 7/2016 | Villemoes | G10L 21/038 |
| 2002/0027962 | A1 | 3/2002 | Muller | |
| 2002/0069051 | A1 | 6/2002 | Hasegawa | |
| 2003/0115042 | A1 * | 6/2003 | Chen | G10L 25/69 |
| | | | | 704/200.1 |
| 2003/0187663 | A1 | 10/2003 | Truman | |
| 2004/0254797 | A1 * | 12/2004 | Niamut | G10L 19/0208 |
| | | | | 704/503 |
| 2004/0267542 | A1 * | 12/2004 | Absar | G10L 19/0208 |
| | | | | 704/500 |
| 2005/0165587 | A1 * | 7/2005 | Cheng | G10L 19/0212 |
| | | | | 702/189 |
| 2007/0027679 | A1 | 2/2007 | Mansour | |
| 2007/0282174 | A1 * | 12/2007 | Sabatino | A61B 7/00 |
| | | | | 600/300 |
| 2008/0065373 | A1 * | 3/2008 | Oshikiri | G10L 19/022 |
| | | | | 704/203 |
| 2008/0091288 | A1 * | 4/2008 | Srinivasan | G10L 19/018 |
| | | | | 700/94 |
| 2008/0112632 | A1 * | 5/2008 | Vos | G10L 19/0017 |
| | | | | 382/248 |
| 2008/0133246 | A1 * | 6/2008 | Fellers | G10L 19/032 |
| | | | | 704/500 |
| 2008/0244220 | A1 * | 10/2008 | Lin | G06F 9/30014 |
| | | | | 712/4 |
| 2008/0312914 | A1 * | 12/2008 | Rajendran | G10L 19/022 |
| | | | | 704/207 |
| 2009/0073006 | A1 * | 3/2009 | Wegener | G10L 19/24 |
| | | | | 341/61 |
| 2009/0192803 | A1 * | 7/2009 | Nagaraja | G10L 19/012 |
| | | | | 704/278 |
| 2009/0198753 | A1 * | 8/2009 | Benjelloun Touimi | G10L 19/0204 |
| | | | | 708/313 |
| 2010/0158269 | A1 * | 6/2010 | Zhang | G10L 21/0208 |
| | | | | 381/94.2 |
| 2010/0274511 | A1 * | 10/2010 | Hirobayashi | G06F 17/141 |
| | | | | 702/76 |
| 2010/0317396 | A1 * | 12/2010 | Reynolds | G10L 19/018 |
| | | | | 455/550.1 |
| 2011/0116639 | A1 * | 5/2011 | Yamada | G10L 19/008 |
| | | | | 381/17 |
| 2011/0153333 | A1 * | 6/2011 | Bessette | G10L 19/26 |
| | | | | 704/500 |
| 2012/0195442 | A1 * | 8/2012 | Villemoes | G10L 21/038 |
| | | | | 381/98 |
| 2015/0058025 | A1 * | 2/2015 | Villemoes | G10L 21/038 |
| | | | | 704/500 |
| 2016/0275965 | A1 * | 9/2016 | Villemoes | G10L 21/038 |

FOREIGN PATENT DOCUMENTS

| | | |
|---|---|---|
| JP | 5237465 | 4/2013 |
| RU | 2256293 | 7/2005 |
| RU | 2006118682 | 12/2007 |
| WO | 98/57436 | 12/1998 |

OTHER PUBLICATIONS

Nagel, F., et al., "A Phase Vocoder Driven Bandwidth Extension Method with Novel Transient Handling for Audio Codecs" AES Convention 126, May 2009.

* cited by examiner

OVERSAMPLING IN A COMBINED TRANSPOSER FILTERBANK

CROSS-REFERENCE TO RELATED APPLICATIONS

This application is a continuation of U.S. patent application Ser. No. 14/505,739 filed Oct. 3, 2014 which is a continuation of U.S. patent application Ser. No. 13/499,893 filed Apr. 2, 2012, which issued as U.S. Pat. No. 8,886,346 on Nov. 11, 2014, which is a National Phase entry of PCT Patent Application Serial No. PCT/EP2010/057156, having international filing date of May 25, 2010 and entitled "Oversampling in a Combined Transposer Filterbank" which claims priority to U.S. Provisional Patent Application No. 61/330,786, filed May 3, 2010 and U.S. Provisional Patent Application No. 61/253,775, filed Oct. 21, 2009. The contents of all of the above applications are incorporated by reference in their entirety for all purposes.

TECHNICAL FIELD

The present invention relates to coding of audio signals, and in particular to high-frequency reconstruction methods including a frequency domain harmonic transposer.

BACKGROUND OF THE INVENTION

HFR technologies, such as the Spectral Band Replication (SBR) technology, allow to significantly improve the coding efficiency of traditional perceptual audio codecs. In combination with MPEG-4 Advanced Audio Coding (AAC), HFR technologies form very efficient audio codecs, which are already in use within the XM Satellite Radio system and Digital Radio Mondiale, and also standardized within 3GPP, DVD Forum and others. The combination of AAC and SBR is called aacPlus. It is part of the MPEG-4 standard where it is referred to as the High Efficiency AAC Profile (HE-AAC). In general, HFR technology can be combined with any perceptual audio codec in a back and forward compatible way, thus offering the possibility to upgrade already established broadcasting systems like the MPEG Layer-2 used in the Eureka DAB system. HFR transposition methods can also be combined with speech codecs to allow wide band speech at ultra low bit rates.

The basic idea behind HRF is the observation that usually a strong correlation between the characteristics of the high frequency range of a signal and the characteristics of the low frequency range of the same signal is present. Thus, a good approximation for a representation of the original input high frequency range of a signal can be achieved by a signal transposition from the low frequency range to the high frequency range.

This concept of transposition was established in WO 98/57436 which is incorporated by reference, as a method to recreate a high frequency band from a lower frequency band of an audio signal. A substantial saving in bit-rate can be obtained by using this concept in audio coding and/or speech coding. In the following, reference will be made to audio coding, but it should be noted that the described methods and systems are equally applicable to speech coding and in unified speech and audio coding (USAC).

In a HFR based audio coding system, a low bandwidth signal is presented to a core waveform coder for encoding, and higher frequencies are regenerated at the decoder side using transposition of the low bandwidth signal and additional side information, which is typically encoded at very low bit-rates and which describes the target spectral shape. For low bit-rates, where the bandwidth of the core coded signal is narrow, it becomes increasingly important to reproduce or synthesize a high band, i.e. the high frequency range of the audio signal, with perceptually pleasant characteristics.

One of the underlying problems that exist with harmonic HFR methods are the opposing constraints of an intended high frequency resolution in order to get a high quality transposition for stationary sounds, and the time response of the system for transient or percussive sounds. In other words, while the use of a high frequency resolution is beneficial for the transposition of stationary signals, such high frequency resolution typically requires large window sizes which are detrimental when dealing with transient portions of a signal. One approach to deal with this problem may be to adaptively change the windows of the transposer, e.g. by using window-switching, as a function of input signal characteristics. Typically long windows will be used for stationary portions of a signal, in order to achieve high frequency resolution, while short windows will be used for transient portions of the signal, in order to implement a good transient response, i.e. a good temporal resolution, of the transposer. However, this approach has the drawback that signal analysis measures such as transient detection or the like have to be incorporated into the transposition system. Such signal analysis measures often involve a decision step, e.g. a decision on the presence of a transient, which triggers a switching of signal processing. Furthermore, such measures typically affect the reliability of the system and they may introduce signal artifacts when switching the signal processing, e.g. when switching between window sizes.

In order to reach improved audio quality and in order to synthesize the required bandwidth of the high band signal, harmonic HFR methods typically employ several orders of transposition. In order to implement a plurality of transpositions of different transposition order, prior art solutions require a plurality of filter banks either in the analysis stage or the synthesis stage or in both stages. Typically, a different filter bank is required for each different transposition order. Moreover, in situations where the core waveform coder operates at a lower sampling rate than the sampling rate of the final output signal, there is typically an additional need to convert the core signal to the sampling rate of the output signal, and this upsampling of the core signal is usually achieved by adding yet another filter bank. All in all, the computationally complexity increases significantly with an increasing number of different transposition orders.

The present document addresses the aforementioned problems regarding the transient performance of harmonic transposition and regarding the computational complexity. As a result, improved harmonic transposition is achieved at a low additional complexity.

SUMMARY OF THE INVENTION

According to an aspect, a system configured to generate a high frequency component of a signal from a low frequency component of the signal is described. The system may comprise an analysis filter bank comprising an analysis transformation unit having a frequency resolution of $\Delta f$. The analysis transformation unit may be configured to perform e.g. a Fourier Transform, a Fast Fourier Transform, a Discrete Fourier Transform or a Wavelet Transform. The analysis filter bank may further comprise an analysis window having a duration of $D_A$. The analysis window may have the shape e.g. of a Gaussian window; a cosine window; a Hamming window; a Hann window; a rectangular window; a Bartlett window; or a Blackman window. The analysis filter bank may be configured to provide a set of analysis subband signals from the low frequency component of the signal.

The system may comprise a nonlinear processing unit configured to determine a set of synthesis subband signals based on a portion of the set of analysis subband signals, wherein the portion of the set of analysis subband signals is phase shifted by a transposition order T. In particular, the subband signals may comprise complex values and the phase shifting may comprise the multiplication of the phase of the complex subband values by the order T.

The system may comprise a synthesis filter bank comprising a synthesis transformation unit having a frequency resolution of $Q\Delta f$. The synthesis transformation unit may be configured to perform the corresponding inverse transform to the transform performed by the analysis transformation unit. Furthermore, the synthesis filter bank may comprise a synthesis window having a duration of $D_S$ and having any of the above listed shapes. Q is a frequency resolution factor with $Q \geq 1$ and smaller than the transposition order T. In a particular embodiment, the frequency resolution factor is selected as $Q>1$. The synthesis filter bank may be configured to generate the high frequency component of the signal from the set of synthesis subband signals.

Typically, the value of the product of the frequency resolution $\Delta f$ and the duration $D_A$ of the analysis filter bank is selected based on the frequency resolution factor Q. In particular, the product $\Delta f D_A$ may be proportional to $$\frac{1}{Q+1}.$$

In an embodiment, the value of product the $\Delta f D_A$ is smaller or equal to $$\frac{2}{Q+1}.$$

Furthermore, the product $\Delta f D_A$ may be greater than $$\frac{2}{T+1}.$$

The value of the product $\Delta f D_A$ of the analysis filter bank may be equal to the value of the product $Q\Delta f D_s$ of the synthesis filter bank. By selecting the analysis and/or the synthesis filter bank according to any of the above rules, artifacts caused by harmonic transposition on transients of the signal may be reduced or completely removed, while allowing a reduced computational complexity of the harmonic transposer.

The system may further comprise a second nonlinear processing unit configured to determine a second set of synthesis subband signals from the set of analysis subband signals using a second transposition order $T_2$; wherein the second set of synthesis subband signals is determined based on a portion of the set of analysis subband signals and wherein the portion of the set of analysis subband signals is phase shifted by the second transposition order $T_2$. The transposition order T and the second transposition order $T_2$ may be different. The system may further comprise a combining unit configured to combine the set of synthesis subband signals and the second set of synthesis subband signals; thereby yielding a combined set of synthesis subband signals as an input to the synthesis filter bank. The combining unit may be configured to add or average corresponding subband signals from the set of synthesis subband signals and the second set of synthesis subband signals. In other words, the combining unit may be configured to superpose synthesis subband signals of the set of synthesis subband signals and the second set of synthesis subband signals corresponding to overlapping frequency ranges.

In an embodiment, the analysis filter bank may have a number $K_A$ of analysis subbands, with $K_A>1$, where k is an analysis subband index with $k=0, \ldots, K_A-1$. The synthesis filter bank may have a number $N_S$ of synthesis subbands, with $N_S>0$, where n is a synthesis subband index with $n=0, \ldots, N_S-1$. In such cases, the nonlinear processing unit may be configured to determine an $n^{th}$ synthesis subband signal of the set of synthesis subband signals from a $k^{th}$ analysis subband signal and a $(k+1)^{th}$ analysis subband signal of the set of analysis subband signals. In particular, the nonlinear processing unit may be configured to determine a phase of the $n^{th}$ synthesis subband signal as the sum of a shifted phase of the $k^{th}$ analysis subband signal and a shifted phase of the $(k+1)^{th}$ analysis subband signal. Furthermore, the nonlinear processing unit may be configured to determine a magnitude of the $n^{th}$ synthesis subband signal as the product of an exponentiated magnitude of the $k^{th}$ analysis subband signal and an exponentiated magnitude of the $(k+1)^{th}$ analysis subband signal.

The analysis subband index k of the analysis subband signal contributing to the synthesis subband with synthesis subband index n may be given by the integer obtained by truncating the expression $$\frac{Q}{T}n;$$

wherein a remainder r may be given by $$\frac{Q}{T}n-k.$$

In such cases, the nonlinear processing unit may be configured to determine the phase of the $n^{th}$ synthesis subband signal as the sum of the phase of the $k^{th}$ analysis subband signal multiplied by $T(1-r)$ and the phase of the $(k+1)^{th}$ analysis subband signal multiplied by $T(r)$, i.e. by performing a linear interpolation of phase. Furthermore, the nonlinear processing unit may be configured to determine the magnitude of the $n^{th}$ synthesis subband signal as the product of the magnitude of the $k^{th}$ analysis subband signal raised to the power of $(1-r)$ and the magnitude of the $(k+1)^{th}$ analysis subband signal raised to the power of r, i.e. by determining the geometrical mean of the magnitudes.

The analysis filter bank and the synthesis filter bank may be evenly stacked such that a center frequency of an analysis subband is given by $k\Delta f$ and a center frequency of a synthesis subband is given by $nQ\Delta f$. In an alternative embodiment, the analysis filter bank and the synthesis filter bank may be oddly stacked such that a center frequency of an analysis subband is given by $(k+\frac{1}{2})\Delta f$ and a center frequency of a synthesis subband is given by $(n+\frac{1}{2})Q\Delta f$; and the difference between the transposition order T and the resolution factor Q is even.

A sampling rate of the low frequency component may be $f_A$. The analysis transformation unit may perform a discrete M point transformation. The analysis window may have a length of $L_A$ samples and/or the analysis window may be shifted by an analysis hop size of $\Delta s_A$ samples along the low frequency component. In such cases, the frequency resolution may be given by $$\Delta f = \frac{f_A}{M},$$

the duration of the analysis window may be given by $$D_A = \frac{L_A}{f_A}$$

and/or a physical time stride of the analysis filter bank may be given by $$\Delta t_A = \frac{\Delta s_A}{f_A}.$$

A sampling rate of the high frequency component may be $f_S = Qf_A$. The synthesis transformation unit may perform a discrete M point transformation, in particular it may perform the respective inverse transformation of the analysis transformation unit. The synthesis window may have a length of $L_S$ samples and/or the synthesis window may be shifted by a synthesis hop size of $\Delta s_S$ samples along the high frequency component. In such cases, the frequency resolution may be given by $$Q\Delta f = \frac{f_S}{M},$$

the duration may be given by $$D_S = \frac{L_S}{f_S}$$

and/or a physical time stride of the synthesis filter bank may be given by $$\Delta t_S = \frac{\Delta s_S}{f_S} = \frac{\Delta s_A}{f_A} = \Delta t_A.$$

According to a further aspect, a system for generating an output signal comprising a high frequency component from an input signal comprising a low frequency component using a transposition order T is described. The system may comprise an analysis window unit configured to apply an analysis window of a length of $L_A$ samples, thereby extracting a frame of the input signal. The system may comprise an analysis transformation unit of order M and having a frequency resolution $\Delta f$ configured to transform the $L_A$ samples into M complex coefficients. The system may comprise a nonlinear processing unit, configured to alter the phase of the complex coefficients by using the transposition order T. The altering of the phase may comprise shifting the phase of the complex coefficients as outlined in the present document. The system may comprise a synthesis transformation unit of order M and having a frequency resolution $Q\Delta f$, configured to transform the altered coefficients into M altered samples; wherein Q is a frequency resolution factor smaller than the transposition order T. Furthermore, the system may comprise a synthesis window unit configured to apply a synthesis window of a length of $L_S$ samples to the M altered samples, thereby generating a frame of the output signal.

M may be based on the frequency resolution factor Q. In particular, the difference between M and the average length of the analysis window and the synthesis window (612) may be proportional to (Q−1). In an embodiment, M is greater or equal to $(QL_A+L_S)/2$. Furthermore, M may be smaller than $(TL_A+L_S)/2$.

According to another aspect, a method for generating a high frequency component of a signal from a low frequency component of the signal is described. The method may comprise the step of providing a set of analysis subband signals from the low frequency component of the signal using an analysis filter bank comprising an analysis transformation unit having a frequency resolution of $\Delta f$ and an analysis window having a duration of $D_A$. Furthermore, the method may comprise the step of determining a set of synthesis subband signals based on a portion of the set of analysis subband signals, wherein the portion of the set of analysis subband signals is phase shifted by a transposition order T. Eventually, the method may comprise the step of generating the high frequency component of the signal from the set of synthesis subband signals using a synthesis filter bank comprising a synthesis transformation unit having a frequency resolution of $Q\Delta f$ and a synthesis window having a duration of $D_S$. Q is a resolution factor with $Q \geq 1$ and smaller than the transposition order T. The value of the product of the frequency resolution $\Delta f$ and the duration $D_A$ of the analysis filter bank may be selected based on the frequency resolution factor Q.

According to a further aspect, a method for generating an output signal comprising a high frequency component from an input signal comprising a low frequency component using a transposition order T is described. The method may comprise the steps of applying an analysis window of a length of $L_A$ samples, comprise the steps of applying an analysis window of a length of $L_A$ samples, thereby extracting a frame of the input signal; and of transforming the frame of $L_A$ samples of the input signal into M complex coefficients using an analysis transformation of order M and frequency resolution $\Delta f$. Furthermore, the method may comprise the step of altering the phase of the complex coefficients by using the transposition order T. The altering of the phase may be performed according to the methods outlined in the present document. In addition, the method may comprise the steps of transforming the altered coefficients into M altered samples using a synthesis transformation of order M and of frequency resolution $Q\Delta f$ wherein Q is a frequency resolution factor smaller than the transposition order T; and of applying a synthesis window of a length of $L_S$ samples to the M altered samples, thereby generating a frame of the output signal. M may be based on the frequency resolution factor Q.

According to another aspect, a method for designing a harmonic transposer configured to generate a high frequency component of a signal from a low frequency component of the signal is described. The method may comprise the step of providing an analysis filter bank comprising an analysis transformation unit having a frequency resolution of $\Delta f$; and an analysis window having a duration of $D_A$; the analysis filter bank being configured to provide a set of analysis subband signals from the low frequency component of the signal. Furthermore, the method may comprise the step of providing a nonlinear processing unit configured to determine a set of synthesis subband signals based on a portion of the set of analysis subband signals, wherein the portion of the set of analysis subband signals is phase shifted by a transposition order T. In addition, the method may comprise the step of providing a synthesis filter bank comprising a synthesis transformation unit having a frequency resolution of $Q\Delta f$; and a synthesis window having a duration of $D_S$; the synthesis filter bank being configured to generate the high frequency component of the signal from the set of synthesis subband signals; wherein Q is a frequency resolution factor with $Q \geq 1$ and smaller than the transposition order T. Furthermore, the method may comprise the step of selecting the value of the product of the frequency resolution $\Delta f$ and the duration $D_A$ of the analysis filter bank based on the frequency resolution factor Q.

According to another aspect, a method for designing a transposer configured to generate an output signal comprising a high frequency component from an input signal comprising a low frequency component using a transposition order T is described. The method may comprise the steps of providing an analysis window unit configured to apply an analysis window of a length of $L_A$ samples, thereby extracting a frame of the input signal; and of providing an analysis transformation unit of order M and having a frequency resolution $\Delta f$ configured to transform the $L_A$ samples into M complex coefficients. Furthermore, the method may comprise the step of providing a nonlinear processing unit, configured to alter the phase of the complex coefficients by using the transposition order T. In addition, the method may comprise the steps of providing a synthesis transformation unit of order M and having a frequency resolution $Q\Delta f$, configured to transform the altered coefficients into M altered samples; wherein Q is a frequency resolution factor smaller than the transposition order T; and of providing a synthesis window unit configured to apply a synthesis window of a length of $L_s$ samples to the M altered samples, thereby generating a frame of the output signal. Eventually, the method may comprise the step of selecting M based on the frequency resolution factor Q.

It should be noted that the methods and systems including its preferred embodiments as outlined in the present patent application may be used stand-alone or in combination with the other methods and systems disclosed in this document. Furthermore, all aspects of the methods and systems outlined in the present patent application may be arbitrarily combined. In particular, the features of the claims may be combined with one another in an arbitrary manner.

BRIEF DESCRIPTION OF THE DRAWINGS

The present invention will now be described by way of illustrative examples, not limiting the scope or spirit of the invention, with reference to the accompanying drawings, in which.

DESCRIPTION OF PREFERRED EMBODIMENTS

The below-described embodiments are merely illustrative for the principles of the present invention for oversampling in a combined transposer filter bank. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

Figure 1:
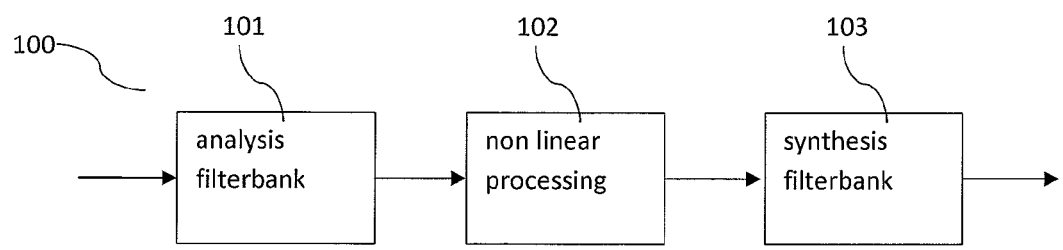
FIG. 1 illustrates the operation of an example single order frequency domain (FD) harmonic transposer.

FIG. 1 illustrates the operation of a frequency domain (FD) harmonic transposer 100. In a basic form, a $T^{th}$ order harmonic transposer is a unit that shifts all signal components H(f) of the input signal, i.e. a subband of the signal in the frequency domain, to H(Tf). I.e. the frequency component H(f) of the input signal is shifted to a T times higher frequency. In order to implement such transposition in the frequency domain, an analysis filter bank 101 transforms the input signal from the time-domain to the frequency domain and outputs complex subbands or subband signals, also referred to as the analysis subbands or analysis subband signals. The analysis filter bank typically comprises an analysis transform, e.g. an FFT, DFT or wavelet transform, and a sliding analysis window. The analysis subband signals are submitted to nonlinear processing 102 modifying the phase and/or the amplitude according to the chosen transposition order T. Typically, the nonlinear processing outputs a number of subband signals which is equal to the number of input subband signals, i.e. equal to the number of analysis subband signals. The modified subbands or subband signals, which are also referred to as the synthesis subbands or synthesis subband signals, are fed to a synthesis filter bank 103 which transforms the subband signals from the frequency domain into the time domain and outputs the transposed time domain signal. The synthesis filter bank 103 typically comprises an inverse transform, e.g. an inverse FFT, inverse DFT or inverse wavelet transform, in combination with a sliding synthesis window.

Typically, each filter bank has a physical frequency resolution $\Delta f$ measured in Hertz and a physical time stride parameter $\Delta t$ measured in seconds, wherein the physical frequency resolution $\Delta f$ is usually associated with the frequency resolution of the transform function and the physical time stride parameter $\Delta t$ is usually associated with the time interval between succeeding window functions. These two parameters, i.e. the frequency resolution and the time stride, define the discrete-time parameters of the filter bank given the chosen sampling rate. By choosing the physical time stride parameters, i.e. the time stride parameter measured in time units e.g. seconds, of the analysis and synthesis filter banks to be identical, an output signal of the transposer 100 may be obtained which has the same sampling rate as the input signal. Furthermore, by omitting the nonlinear processing 102 a perfect reconstruction of the input signal at the output may be achieved. This requires a careful design of the analysis and synthesis filter banks. On the other hand, if the output sampling rate is chosen to be different from the input sampling rate, a sampling rate conversion may be obtained. This mode of operation may be necessary in the case where the desired bandwidth of the output signal y is larger than half of sampling rate of the input signal x, i.e. when the desired output bandwidth exceeds the Nyqvist frequency of the input signal.

Figure 2:
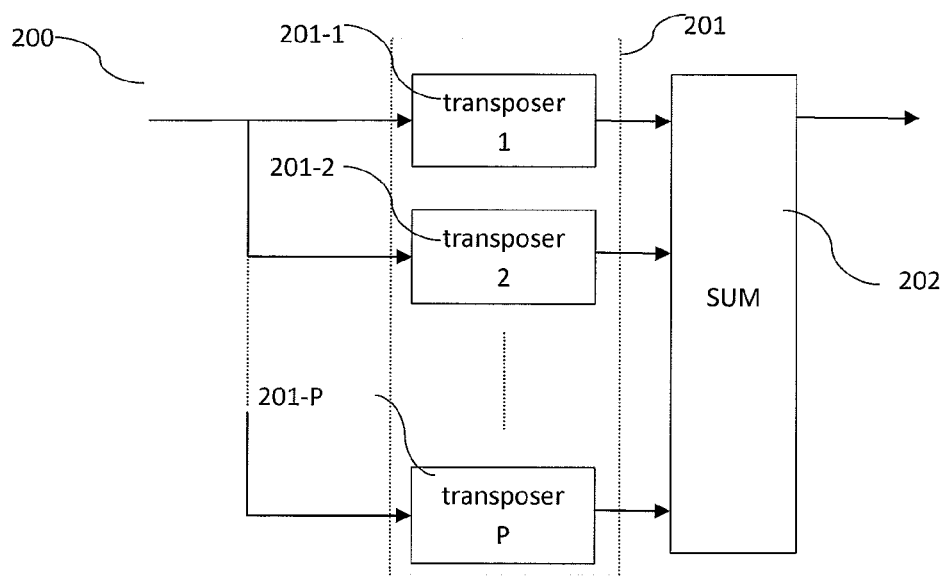
FIG. 2 illustrates the operation of an example harmonic transposer using several orders.

FIG. 2 illustrates the operation of a multiple transposer or multiple transposer system 200 comprising several harmonic transposers 201-1, . . . , 201-P of different orders. The input signal which is to be transposed is passed to a bank of P individual transposers 201-1, 201-2, . . . , 201-P. The individual transposers 201-1, 201-2, . . . , 201-P perform a harmonic transposition of the input signal as outlined in the context of FIG. 1. Typically, each of the individual transposers 201-1, 201-2, . . . , 201-P performs a harmonic transposition of a different transposition order T. By way of example, transposer 201-1 may perform a transposition of order T=1, transposer 201-2 may perform a transposition of order T=2, . . . , and transposer 201-P may perform a transposition of order T=P. However, in generic terms, any of the transposers 201-1, . . . , 201-P may perform a harmonic transposition of an arbitrary transposition order T. The contributions, i.e. the output signals of the individual transposers 201-1, 201-2, . . . , 201-P may be summed in the combiner 202 to yield the combined transposer output.

It should be noted that each transposer 201-1, 201-2, . . . , 201-P requires an analysis and a synthesis filter bank as depicted in FIG. 1. Moreover, the usual implementation of the individual transposers 201-1, 201-2, . . . , 201-P will typically change the sampling rate of the processed input signal by different amounts. By way of example, the sampling rate of the output signal of the transposer 201-P may be T times higher than the sampling rate of the input signal to the transposer 201-P, wherein T is the transposition order applied by the transposer 201-P. This may be due to a bandwidth expansion factor of T used within the transposer 201-P, i.e. due to the use of a synthesis filter bank which has T times more subchannels than the analysis filter bank. By doing this the sampling rate and the Nyqvist frequency is increased by a factor T. As a consequence, the individual time domain signals may need to be resampled in order to allow for a combining of the different output signals in the combiner 202. The resampling of the time domain signals can be carried out on the input side or on the output side of each individual transposer 201-1, 201-2, . . . , 201-P.

Figure 3:
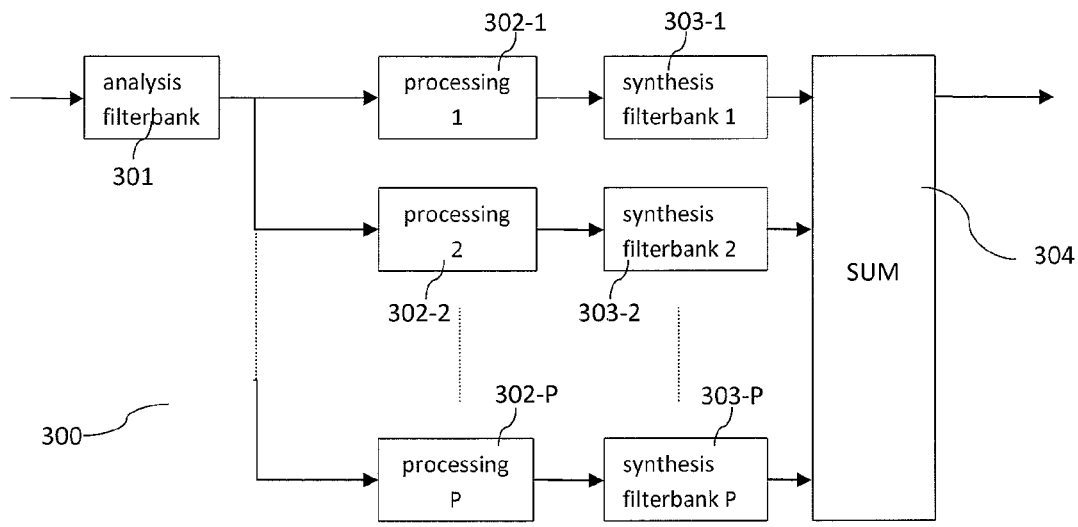
FIG. 3 illustrates prior art operation of an example harmonic transposer using several orders of transposition, while using a common analysis filter bank.

FIG. 3 illustrates an exemplary configuration of a multiple harmonic transposer or multiple transposer system 300 performing several orders of transposition and using a common analysis filter bank 301. A starting point for the design of the multiple transposer 300 may be to design the individual transposers 201-1, 201-2, . . . , 201-P of FIG. 2 such that the analysis filter banks (reference sign 101 in FIG. 1) of all transposers 201-1, 201-2, . . . , 201-P are identical and can be replaced by a single analysis filter bank 301. As a consequence, the time domain input signal is transformed into a single set of frequency domain subband signals, i.e. a single set of analysis subband signals. These subband signals are submitted to different nonlinear processing units 302-1, 302-2, . . . , 302-P for different orders of transposition. As outlined above in the context of FIG. 1 each nonlinear processing unit performs a modification of the phase and/or amplitude of the subband signals and this modification differs for different orders of transposition. Subsequently, the differently modified subband signals or subbands have to be submitted to different synthesis filter banks 303-1, 303-2, . . . , 303-P corresponding to the different nonlinear processing units 302-1, 302-2, . . . , 302-P. As an outcome, P differently transposed time domain output signals are obtained which are summed in the combiner 304 to yield the combined transposer output.

It should be noted that if the synthesis filter banks 303-1, 303-2, . . . , 303-P corresponding to the different transposition orders operate at different sampling rates, e.g. by using different degrees of bandwidth expansion, the time domain output signals of the different synthesis filter banks 303-1, 303-2, . . . , 303-P need to be differently resampled in order to align the P output signals to a common time grid, prior to their summation in combiner 304.

Figure 4:
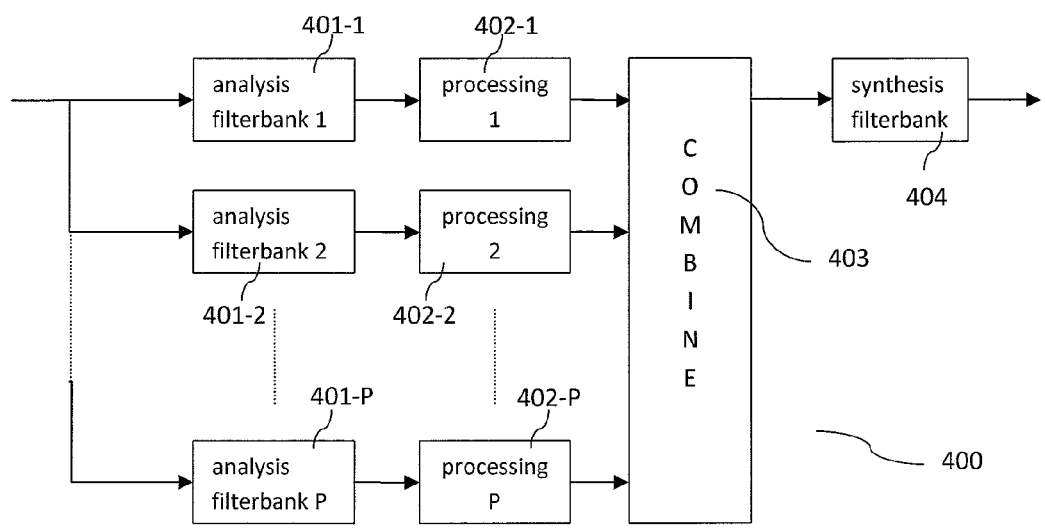
FIG. 4 illustrates prior art operation of an example harmonic transposer using several orders of transposition, while using a common synthesis filter bank.

FIG. 4 illustrates an example operation of a multiple harmonic transposer 400 using several orders of transposition, while using a common synthesis filter bank 404. The starting point for the design of such a multiple transposer 400 may be the design of the individual transposers 201-1, 201-2, . . . , 200-P of FIG. 1 such that the synthesis filter banks of all transposers are identical and can be replaced by a single synthesis filter bank 404. It should be noted that in an analogous manner as in the situation shown in FIG. 3, the nonlinear processing units 402-1, 402-2, . . . , 402-P are different for each transposition order. Furthermore, the analysis filter banks 401-1, 401-2, . . . , 401-P are different for the different transposition orders. As such, a set of P analysis filter banks 401-1, 401-2, . . . , 401-P determines P sets of analysis subband signals. These P sets of analysis subband signals are submitted to corresponding nonlinear processing units 402-1, 402-2, . . . , 402-P to yield P sets of modified subband signals. These P sets of subband signals may be combined in the frequency domain in the combiner 403 to yield a combined set of subband signals as an input to the single synthesis filter bank 404. This combination in combiner 403 may comprise the feeding of differently processed subband signals into different subband ranges and/or the superposing of contributions of subband signals to overlapping subband ranges. In other words, different analysis subband signals which have been processed with different transposition orders may cover overlapping frequency ranges. By way of example, a second order transposer may transpose the analysis subband [2A,2B] to the subband range [4A,4B]. At the same time, a fourth order transposer may transpose the analysis subband [A,B] to the same subband range [4A,4B]. In such cases, the superposing contributions may be combined, e.g. added and/or averaged, by the combiner 403. The time domain output signal of the multiple transposer 400 is obtained from the common synthesis filter bank 404. In a similar manner as outlined above, if the analysis filter banks 401-1, 401-2, . . . , 401-P operate at different sampling rates, the time domain signals input to the different analysis filter banks 401-1, 401-2, . . . , 401-P may need to be resampled in order to align the output signals of the different nonlinear processing units 402-1, 402-2, . . . , 402-P to the same time grid.

Figure 5:
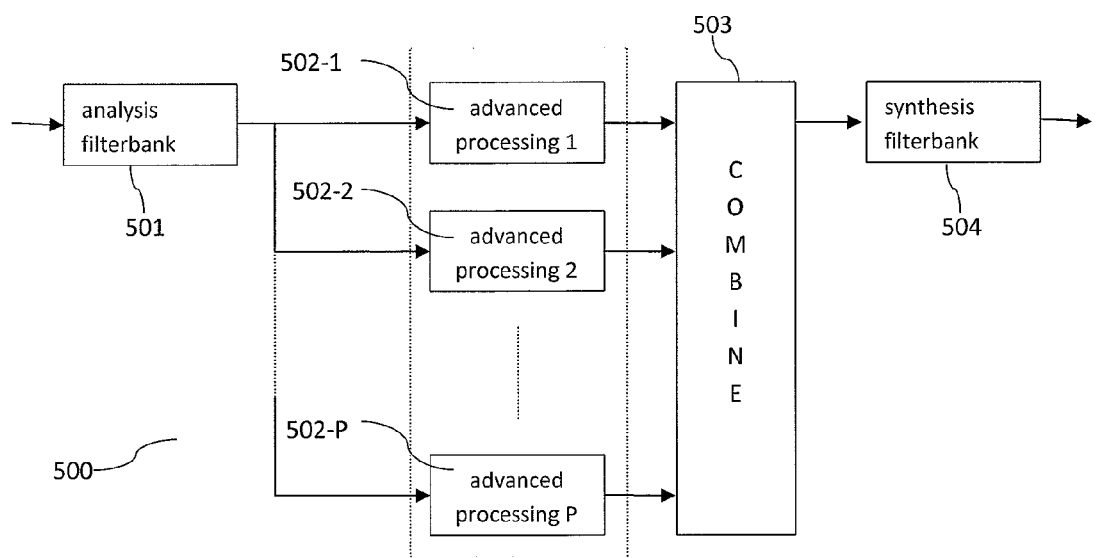
FIG. 5 illustrates the operation of an example harmonic transposer using several orders of transposition, while using a common synthesis filter bank and a common synthesis filter bank.

FIG. 5 illustrates the operation of a multiple harmonic transposer 500 using several orders of transposition and comprising a single common analysis filter bank 501 and a single common synthesis filter bank 504. In this case, the individual transposers 201-1, 201-2, . . . , 201-P of FIG. 2 should be designed such that both, the analysis filter banks and the synthesis filter banks of all the P harmonic transposers are identical. If the condition of identical analysis and synthesis filter banks for the different P harmonic transposers is met, then the identical filter banks can be replaced by a single analysis filter bank 501 and a single synthesis filter bank 504. The advanced nonlinear processing units 502-1, 502-2, . . . , 502-P output different contributions to partly overlapping frequency ranges that are combined in the combiner 503 to yield a combined input to the respective subbands of the synthesis filter bank 504. Similarly to the multiple harmonic transposer 400 depicted in FIG. 4, the combination in the combiner 503 may comprise the feeding of the different output signals of the plurality of nonlinear processing units 502-1, 502-2, . . . , 502-P into different subband ranges, and the superposing of multiple contributing outputs to overlapping subband ranges.

As already indicated above, the nonlinear processing 102 typically provides a number of subbands at its output which corresponds to the number of subbands at the input. The non-linear processing 102 typically modifies the phase and/or the amplitude of the subband or the subband signal according to the underlying transposition order T. By way of example a subband at the input is converted to a subband at the output with T times higher frequency, i.e. a subband at the input to the nonlinear processing 102, i.e. the analysis subband, $[(k-\frac{1}{2})\Delta f, (k+\frac{1}{2})\Delta f]$ may be transposed to a subband at the output of the nonlinear processing 102, i.e. the synthesis subband, $[(k-\frac{1}{2})T\Delta f, (k+\frac{1}{2})T\Delta f]$, wherein k is a subband index number and $\Delta f$ if the frequency resolution of the analysis filter bank. In order to allow for the use of common analysis filter banks 501 and common synthesis filter banks 504, one or more of the advanced processing units 502-1, 502-2, . . . , 502-P may be configured to provide a number of output subbands which may be different from the number of input subbands.

In the following, the principles of advanced nonlinear processing in the nonlinear processing units 502-1, 502-2, . . . , 502-P will be outlined. For this purpose, it is assumed that
 the analysis filter bank and the synthesis filter bank share the same physical time stride parameter $\Delta t$.
 the analysis filter bank has a physical frequency resolution $\Delta f$.
 the synthesis filter bank has a physical frequency resolution $Q\Delta f$ where the resolution factor $Q \geq 1$ is an integer.

Furthermore, it is assumed that the filter banks are evenly stacked, i.e. the subband with index zero is centered around the zero frequency, such that the analysis filter bank center frequencies are given by $k\Delta f$ where the analysis subband index $k=1, \ldots, K_A-1$ and $K_A$ is the number of subbands of the analysis filter bank. The synthesis filter bank center frequencies are given by $kQ\Delta f$ where the synthesis subband index $n=1, \ldots, N_S-1$ and $N_S$ is the number of subbands of the synthesis filter bank.

When performing a conventional transposition of integer order $T \geq 1$ as shown in FIG. 1, the resolution factor Q is selected as Q=T and the nonlinearly processed analysis subband k is mapped into the synthesis subband with the same index n=k. The nonlinear processing 102 typically comprises multiplying the phase of a subband or subband signal by the factor T. I.e. for each sample of the filter bank subbands one may write $$\theta_S(k)=T\theta_A(k), \quad (1)$$

where $\theta_A(k)$ is the phase of a (complex) sample of the analysis subband k and $\theta_S(k)$ is the phase of a (complex) sample of the synthesis subband k. The magnitude or amplitude of a sample of the subband may be kept unmodified or may be increased or decreased by a constant gain factor. Due to the fact that T is an integer, the operation of equation (1) is independent of the definition of the phase angle.

In conventional multiple transposers, the resolution factor Q of an analysis/synthesis filter bank is selected to be equal to the transposition order T of the respective transposer, i.e. Q=T. In this case, the frequency resolution of the synthesis filter bank is $T\Delta f$ and therefore depends on the transposition order T. Consequently, it is necessary to use different filter banks for different transposition orders T either in the analysis or synthesis stage. This is due to the fact that the transposition order T defines the quotient of physical frequency resolutions, i.e. the quotient of the frequency resolution $\Delta f$ of the analysis filter bank and the frequency resolution $T\Delta f$ of the synthesis filter bank.

In order to be able to use a common analysis filter bank 501 and a common synthesis filter bank 504 for a plurality of different transposition orders T, it is proposed to set the frequency resolution of the synthesis filter bank 504 to $Q\Delta f$, i.e. it is proposed to make the frequency resolution of the synthesis filter bank 504 independent of the transposition order T. Then the question arises of how to implement a transposition of order T when the resolution factor Q, i.e. the quotient Q of the physical frequency resolution of the analysis and synthesis filter bank, does not necessarily obey the relation Q=T.

As outlined above, a principle of harmonic transposition is that the input to the synthesis filter bank subband n with center frequency $nQ\Delta f$ is determined from an analysis subband at a T times lower center frequency, i.e. at the center frequency $nQ\Delta f/T$. The center frequencies of the analysis subbands are identified through the analysis subband index k as $k\Delta f$. Both expressions for the center frequency of the analysis subband index, i.e. $nQ\Delta f/T$ and $k\Delta f$, may be set equal. Taking into account that the index n is an integer value, the expression $$\frac{nQ}{T}$$

is a rational number which can be expressed as the sum of an integer analysis subband index k and a remainder $r \in \{0, 1/T, 2/T, \ldots, (T-1)/T\}$ such that $$\frac{nQ}{T} = k + r. \quad (2)$$

As such, it may be stipulated that the input to a synthesis subband with synthesis subband index n may be derived, using a transposition of order T, from the analysis subband with the index k given by equation (2). In view of the fact that $$\frac{nQ}{T}$$

is a rational number, the remainder r may be unequal to 0 and the value k+r may be greater than the analysis subband index k and smaller than the analysis subband index k+1, i.e. k≤k+r≤k+1. Consequently, the input to a synthesis subband with synthesis subband index n should be derived, using a transposition of order T, from the analysis subbands with the analysis subband index k and k+1, wherein k is given by equation (2). In other words, the input of a synthesis subband may be derived from two consecutive analysis subbands.

As an outcome of the above, the advanced nonlinear processing performed in a nonlinear processing unit 502-1, 502-2, . . . , 502-P may comprise the step of considering two neighboring analysis subbands with index k and k+1 in order to provide the output for synthesis subband n. For a transposition order T, the phase modification performed by the nonlinear processing unit 502-1, 502-2, . . . , 502-P may for example be defined by the linear interpolation rule, $$\theta_S(n)=T(1-r)\theta_A(k)+Tr\theta_A(k+1), \quad (3)$$

where $\theta_A(k)$ is the phase of a sample of the analysis subband k, $\theta_A(k+1)$ is the phase of a sample of the analysis subband k+1, and $\theta_S(n)$ is the phase of a sample of the synthesis subband n. If the remainder r is close to zero, i.e. if the value k+r is close to k, then the main contribution of the phase of the synthesis subband sample is derived from the phase of the analysis subband sample of subband k. On the other hand, if the remainder r is close to one, i.e. if the value k+r is close to k+1, then the main contribution of the phase of the synthesis subband sample is derived from the phase of the analysis subband sample of subband k+1. It should be noted that the phase multipliers T(1−r) and Tr are both integers such that the phase modifications of equation (3) are well defined and independent of the definition of the phase angle.

Concerning the magnitudes of the subband samples, the following geometrical mean value may be selected for the determination of the magnitude of the synthesis subband samples, $$a_S(n)=a_A(k)^{(1-r)}a_A(k+1)^r, \quad (4)$$

where $a_S(n)$ denotes the magnitude of a sample of the synthesis subband n, $a_A(k)$ denotes the magnitude of a sample of the analysis subband k and $a_A(k+1)$ denotes the magnitude of a sample of the analysis subband k+1. It should be noted that other interpolation rules for the phase and/or the magnitude may be contemplated.

For the case of an oddly stacked filter bank where the analysis filter bank center frequencies are given by $(n+\frac{1}{2})\Delta f$ with k=1, . . . , $K_A$−1 and the synthesis filter bank center frequencies are given by $$\left(n+\frac{1}{2}\right)\frac{Q\Delta f}{T}$$

with n=1, . . . , $N_S$−1, an corresponding equation to equation (2) may be derived by equating the transposed synthesis filter bank center frequency $$\left(n+\frac{1}{2}\right)\frac{Q\Delta f}{T}$$

and the analysis filter bank center frequency $(k+\frac{1}{2})\Delta f$. Assuming an integer index k and a remainder r∈[0,1[ the following equation for oddly stacked filter banks can be derived:

$$\left(n+\frac{1}{2}\right)\frac{Q}{T} = k+\frac{1}{2}+r. \quad (5)$$

The skilled person will appreciate that if T−Q, i.e. the difference between the transposition order and the resolution factor, is even, T(1−r) and Tr are both integers and the interpolation rules of equations (3) and (4) can be used.

Figure 5B:
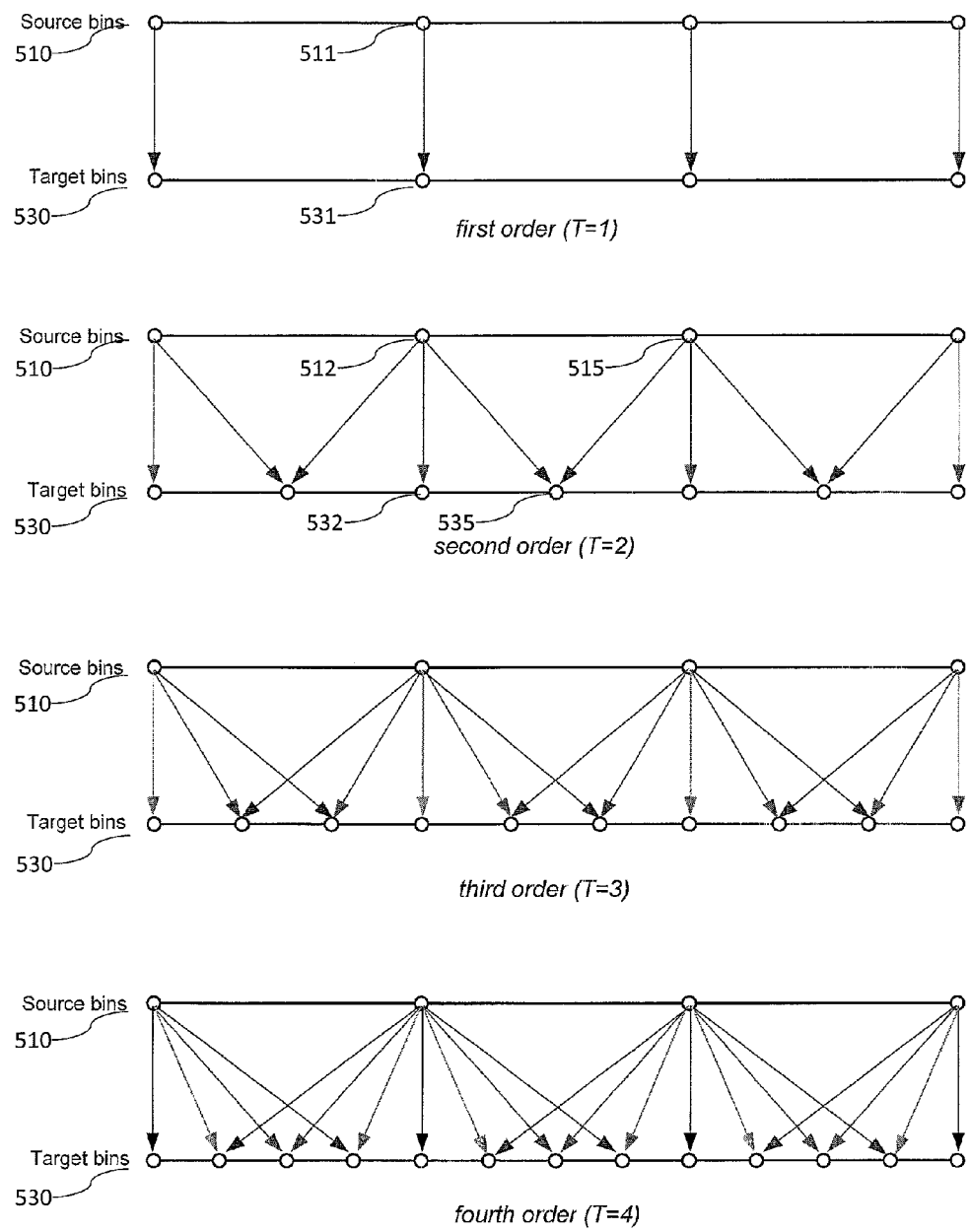
FIG. 5b illustrates an example for the mapping of subband signals for a multiple transposer scheme according to FIG. 5.

The mapping of analysis subbands into synthesis subbands is illustrated in FIG. 5*b*. FIG. 5*b* shows four diagrams for different transposition orders T=1 to T=4. Each diagram illustrates how the source bins 510, i.e. the analysis subbands, are mapped into target bins 530, i.e. synthesis subbands. For ease of illustration, it is assumed that the resolution factor Q is equal to one. In other words, FIG. 5*b* illustrates the mapping of analysis subband signals to synthesis subband signals using Eq. (2) and (3). In the illustrated example the analysis/synthesis filter bank is evenly stacked, with Q=1 and the maximum transposition order T=4.

In the illustrated case, equation (2) may be written as $$\frac{n}{T} = k+r.$$

Consequently, for a transposition order T=1, an analysis subband with an index k is mapped to a corresponding synthesis subband n and the remainder r is always zero. This can be seen in FIG. 5*b* where for example source bin 511 is mapped one to one to a target bin 531.

In case of transposition order T=2, the remainder r takes on the values 0 and ½ and a source bin is mapped to a plurality of target bins. When reversing the perspective, it may be stated that each target bin 532, 535 receives a contribution from up to two source bins. This can be seen in FIG. 5*b*, where the target bin 535 receives a contribution from source bins 512 and 515. However, the target bin 532 receives a contribution from source bin 512 only. If it is assumed that target bin 532 has an even index n, e.g. n=10, then equation (2) specifies that target bin 532 receives a contribution from the source bin 512 with an index k=n/2, e.g. k=5. The remainder r is zero, i.e. there is no contribution from the source bin 515 with index k+1, e.g. k+1=6. This changes for target bin 535 with an uneven index n, e.g. n=11. In this case, equation (2) specifies that target bin 535 receives contributions from the source bin 512 (index k=5) and source bin 515 (index k+1=6). This applies in a similar manner to higher transposition orders T, e.g. T=3 and T=4, as shown in FIG. 5*b*.

A further interpretation of the above advanced nonlinear processing may be as follows. The advanced nonlinear processing may be understood as a combination of a transposition of a given order T into intermediate subband signals on an intermediate frequency grid TΔf, and a subsequent mapping of the intermediate subband signals to a frequency grid defined by a common synthesis filter bank, i.e. by a frequency grid QΔf. In order to illustrate this interpretation, reference is made again to FIG. 5b. However, for this illustration, the source bins 510 are considered to be intermediate subbands derived from the analysis subbands using an order of transposition T. These intermediate subbands have a frequency grid given by TΔf. In order to generate synthesis subband signals on a pre-defined frequency grid QΔf given by the target bins 530, the source bins 510, i.e. the intermediate subbands having the frequency grid TΔf, need to be mapped onto the pre-defined frequency grid QΔf. This can be performed by determining a target bin 530, i.e. a synthesis subband signal on the frequency grid QΔf, by interpolating one or two source bins 510, i.e. intermediate subband signals on the frequency grid TΔf. In a preferred embodiment, linear interpolation is used, wherein the weights of the interpolation are inversely proportional to the difference between the center frequency of the target bin 530 and the corresponding source bin 510. By way of example, if the difference is zero, then the weight is 1, and if the difference is TΔf then the weight is 0.

In summary, a nonlinear processing method has been described which allows the determination of contributions to a synthesis subband by means of transposition of several analysis subbands. The nonlinear processing method enables the use of single common analysis and synthesis subband filter banks for different transposition orders, thereby significantly reducing the computational complexity of multiple harmonic transposers.

Figure 6A:
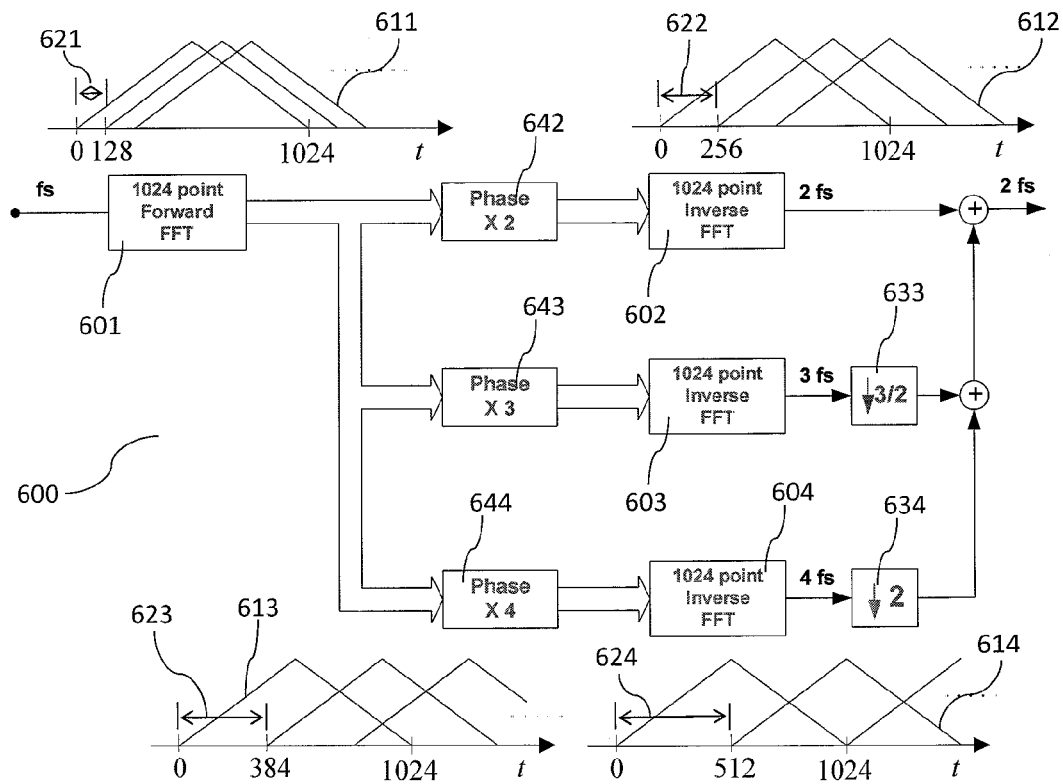
FIG. 6a illustrates an example multiple transposer of order T=2, 3, 4 using a common analysis filter bank and separate synthesis filter banks.
Figure 6B:
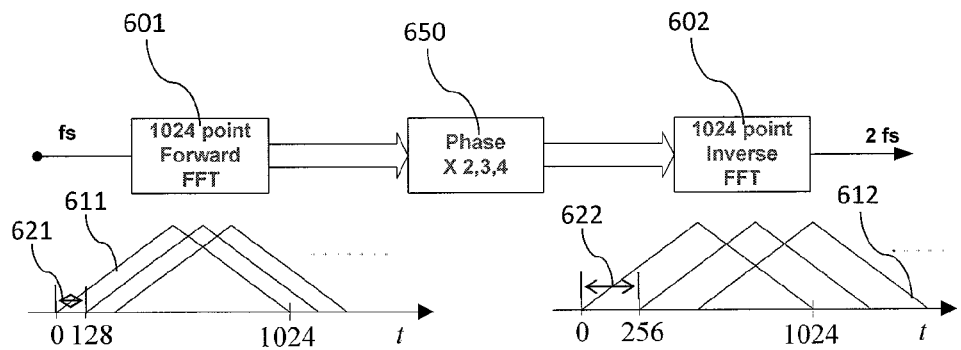
FIG. 6b illustrates an example multiple transposer of order T=2, 3, 4 using a common analysis filter bank and a common synthesis filter bank.

FIGS. 6a and 6b illustrate example analysis/synthesis filter banks using a M=1024 point FFT/DFT (Fast Fourier Transform or Discrete Fourier Transform) for multiple transposition orders of T=2, 3, 4. FIG. 6a illustrates the conventional case of a multiple harmonic transposer 600 using a common analysis filter bank 601 and separate synthesis filter banks 602, 603, 604 for each transposition factor T=2, 3, 4. FIG. 6a shows the analysis windows $v_A$ 611 and the synthesis windows $v_S$ 612, 613, 614 applied at the analysis filter bank 601 and the synthesis filter banks 602, 603, 604, respectively. In the illustrated example, the analysis window $v_A$ 611 has a length $L_A$=1024 which is equal to the size M of the FFT or DFT of the analysis/synthesis filter banks 601, 602, 603, 604. In a similar manner, the synthesis windows $v_S$ 612, 613, 614 have a length of $L_S$=1024 which is equal to the size M of the FFT or DFT.

FIG. 6a also illustrates the hop size $\Delta s_A$ employed by the analysis filter bank 601 and the hop size $\Delta s_S$ employed the synthesis filter banks 602, 603, 604, respectively. The hop size Δs corresponds to the number of data samples by which the respective window 611, 612, 613, 614 is moved between successive transformation steps. The hop size Δs relates to the physical time stride Δt via the sampling rate of the underlying signal, i.e. $\Delta s=f_s \Delta t$, wherein $f_s$ is the sampling rate.

It can be seen that the analysis window 611 is moved by a hop size 621 of 128 samples. The synthesis window 612 corresponding to a transposition of order T=2 is moved by a hop size 622 of 256 samples, i.e. a hop size 622 which is twice the hop size 621 of the analysis window 611. As outlined above, this leads to a time stretch of the signal by the factor T=2. Alternatively, if a T=2 times higher sampling rate is assumed, the difference between the analysis hop size 621 and the synthesis hop size 622 leads to a harmonic transposition of order T=2. I.e. a time stretch by an order T may be converted into a harmonic transposition by performing a sampling rate conversion of order T.

In a similar manner, it can be seen that the synthesis hop size 623 associated with the harmonic transposer of order T=3 is T=3 times higher than the analysis hop size 621, and the synthesis hop size 624 associated with the harmonic transposer of order T=4 is T=4 times higher than the analysis hop size 621. In order to align the sampling rates of the $3^{rd}$ order transposer and the $4^{th}$ order transposer with the output sampling rate of the $2^{nd}$ order transposer, the $3^{rd}$ order transposer and the $4^{th}$ order transposer comprise a factor 3/2—downsampler 633 and a factor 2—downsampler 634, respectively. In general terms, the $T^{th}$ order transposer would comprise a factor T/2—downsampler, if an output sampling rate is requested, which is 2 times higher than the input sampling rate. I.e. no downsampling is required for the harmonic transposer of order T=2.

Finally, FIG. 6a illustrates the separate phase modification units 642, 643, 644 for the transposition order T=2, 3, 4, respectively. These phase modification units 642, 643, 644 perform a multiplication of the phase of the respective subband signals by the transposition order T=2, 3, 4, respectively (see Equation (1)).

An efficient combined filter bank structure for the transposer can be obtained by limiting the multiple transposer of FIG. 6a to a single analysis filter bank 601 and a single synthesis filter bank 602. The $3^{rd}$ and $4^{th}$ order harmonics are then produced in a non-linear processing unit 650 within a $2^{nd}$ order filter bank as depicted in FIG. 6b. FIG. 6b shows an analysis filter bank comprising a 1024 point forward 1–FT unit 601 and an analysis window 611 which is applied on the input signal x with an analysis hop size 621. The synthesis filter bank comprises a 1024 point inverse FFT unit 602 and a synthesis window 612 which is applied with a synthesis hop size 622. In the illustrated example the synthesis hop size 622 is twice the analysis hop size 621. Furthermore, the sampling rate of the output signal y is assumed to be twice the sampling rate of the input signal x.

The analysis/synthesis filter bank of FIG. 6b comprises a single analysis filter bank and a single synthesis filter bank. By using advanced nonlinear processing 650 in accordance to the methods outlined in the context of FIG. 5 and FIG. 5b, i.e. the advanced non-linear processing performed in the units 502-1, . . . , 502-P, this analysis/synthesis filter bank may be used to provide a multiple transposer, i.e. a harmonic transposer for a plurality of transposition orders T.

Figure 7:
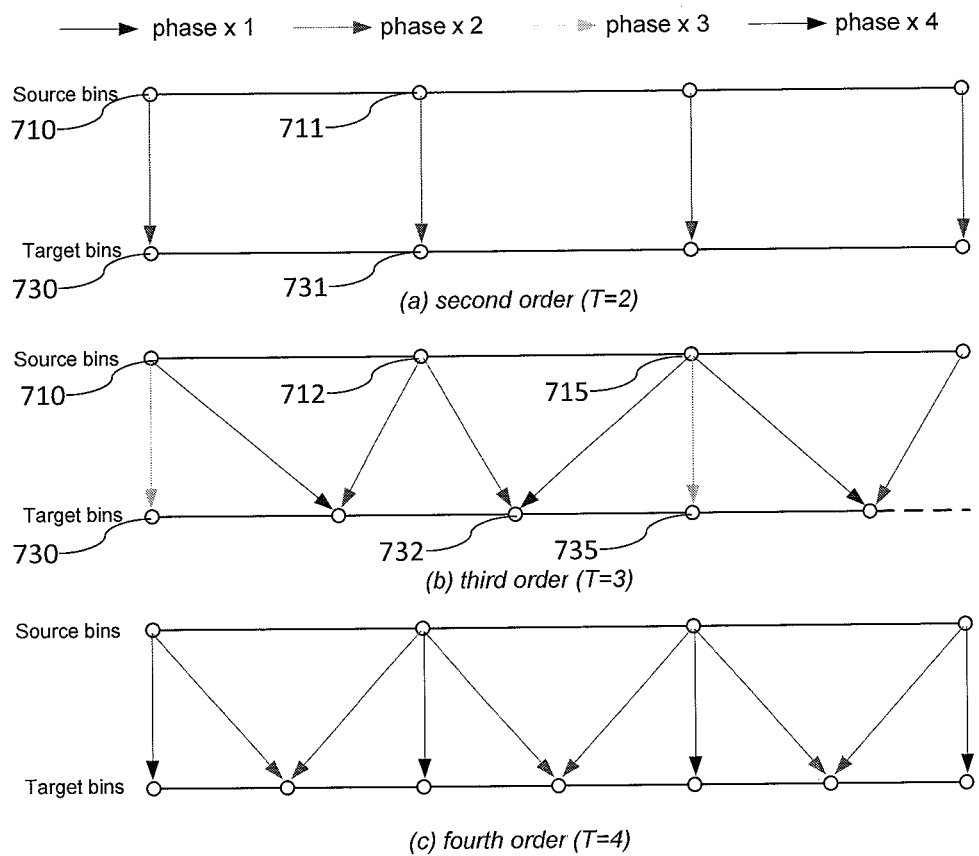
FIG. 7 illustrates an example for the mapping of subband signals for a multiple transposer according to FIG. 6b.

As has been outlined in the context of FIGS. 5 and 5b, the one-to-one mapping of analysis subbands to corresponding synthesis subbands involving a multiplication of the phase of the subband signals by the respective transposition order T, may be generalized to interpolation rules (see Equations (3) and (4)) involving one or more subband signals. It has been outlined that if the physical spacing QΔf of the synthesis filter bank subbands is Q times the physical spacing Δf of the analysis filter bank, the input to the synthesis band with index n is obtained from the analysis bands with indices k and k+1. The relationship between the indexes n and k is given by Equation (2) or (5), depending on whether the filter banks are evenly or unevenly stacked. A geometrical interpolation for the magnitudes is applied with powers 1−r and r (Equation (4)) and the phases are linearly combined with weights T(1−r) and Tr (Equation (3)). For the illustrated case where Q=2, the phase mappings for each transposition factor are illustrated graphically in FIG. 7.

In a similar manner to the case of Q=1 illustrated in FIG. 5, a target subband or target bin 730 receives contributions from up to two source subbands or source bins 710. In the case T=Q=2, each phase modified source bin 711 is assigned to a corresponding target bin 731. For higher transposition orders T>Q, a target bin 735 may be obtained from one corresponding phase modified source bin 715. This is the case if the remainder r obtained from Equation (2) or (5) is zero. Otherwise, a target bin 732 is obtained by interpolating two phase modified source bins 712 and 715.

The above mentioned non-linear processing is performed in the multiple transposer unit 650 which determines target bins 730 for the different orders of transposition T=2, 3, 4 using advanced non-linear processing units 502-2, 502-3, 502-4. Subsequently, corresponding target bins 730 are combined in a combiner unit 503 to yield a single set of synthesis subband signals which are fed to the synthesis filter bank. As outlined above, the combiner unit 503 is configured to combine a plurality of contributions in overlapping frequency ranges from the output of the different non-linear processing units 502-2, 502-3, 502-4.

In the following, the harmonic transposition of transient signals using harmonic transposers is outlined. In this context, it should be noted that harmonic transposition of order T using analysis/synthesis filter banks may be interpreted as time stretching of an underlying signal by an integer transposition factor T followed by a downsampling and/or sample rate conversion. The time stretching is performed such that frequencies of sinusoids which compose the input signal are maintained. Such time stretching may be performed using the analysis/synthesis filter bank in combination with intermediate modification of the phases of the subband signals based on the transposition order T. As outlined above, the analysis filter bank may be a windowed DFT filter bank with analysis window $v_A$ and the synthesis filter bank may be a windowed inverse DFT filter bank with synthesis window $v_S$. Such analysis/synthesis transform is also referred to as short-time Fourier Transform (STFT).

A short-time Fourier transform is performed on a time-domain input signal x to obtain a succession of overlapped spectral frames. In order to minimize possible side-band effects, appropriate analysis/synthesis windows, e.g. Gaussian windows, cosine windows, Hamming windows, Hann windows, rectangular windows, Bartlett windows, Blackman windows, and others, should be selected.

The time delay at which every spectral frame is picked up from the input signal x is referred to as the hop size $\Delta s$ or physical time stride $\Delta t$. The STFT of the input signal x is referred to as the analysis stage and leads to a frequency domain representation of the input signal x. The frequency domain representation comprises a plurality of subband signals, wherein each subband signal represents a certain frequency component of the input signal.

For the purpose of time-stretching of the input signal, each subband signal may be time-stretched, e.g. by delaying the subband signal samples. This may be achieved by using a synthesis hop-size which is greater than the analysis hop-size. The time domain signal may be rebuilt by performing an inverse (Fast) Fourier transform on all frames followed by a successive accumulation of the frames. This operation of the synthesis stage is referred to as overlap-add operation. The resulting output signal is a time-stretched version of the input signal comprising the same frequency components as the input signal. In other words, the resulting output signal has the same spectral composition as the input signal, but it is slower than the input signal i.e. its progression is stretched in time.

The transposition to higher frequencies may then be obtained subsequently, or in an integrated manner, through downsampling of the stretched signals or by performing a sample-rate conversion of the time stretched output signal. As a result the transposed signal has the length in time of the initial signal, but comprises frequency components which are shifted upwards by a pre-defined transposition factor.

In view of the above, the harmonic transposition of transient signals using harmonic transposers is described by considering as a starting point the time stretching of a prototype transient signal, i.e. a discrete time Dirac pulse at time instant $t=t_0$, $$\delta(t - t_0) = \begin{cases} 1, t = t_0 \\ 0, t \neq t_0 \end{cases}.$$

The Fourier transform of such a Dirac pulse has unit magnitude and a linear phase with a slope proportional to $t_0$:

$$X(\Omega_m) = \sum_{n=-\infty}^{\infty} \delta(n - t_0)\exp(-j\Omega_m n) = \exp(-j\Omega_m t_0),$$

wherein $$\Omega_m = 2\pi \frac{m}{M}$$

is the center frequency of the $m^{th}$ subband signal of the STFT analysis and M is the size of the discrete Fourier transform (DFT). Such Fourier transform can be considered as the analysis stage of the analysis filter bank described above, wherein a flat analysis window $v_A$ of infinite duration is used. In order to generate an output signal y which is time-stretched by a factor T, i.e. a Dirac pulse $\delta(t-Tt_0)$ at the time instant $t=Tt_0$, the phase of the analysis subband signals should be multiplied by the factor T in order to obtain the synthesis subband signal $Y(\Omega_m)=\exp(-j\Omega_m Tt_0)$ which yields the desired Dirac pulse $\delta(t-Tt_0)$ as an output of an inverse Fourier Transform.

However, it should be noted that the above considerations refer to an analysis/synthesis stage using analysis and synthesis windows of infinite lengths. Indeed, a theoretical transposer with a window of infinite duration would give the correct stretch of a Dirac pulse $\delta(t-t_0)$. For a finite duration windowed analysis, the situation is scrambled by the fact that each analysis block is to be interpreted as one period interval of a periodic signal with a period equal to the size of the DFT.

Figure 8:
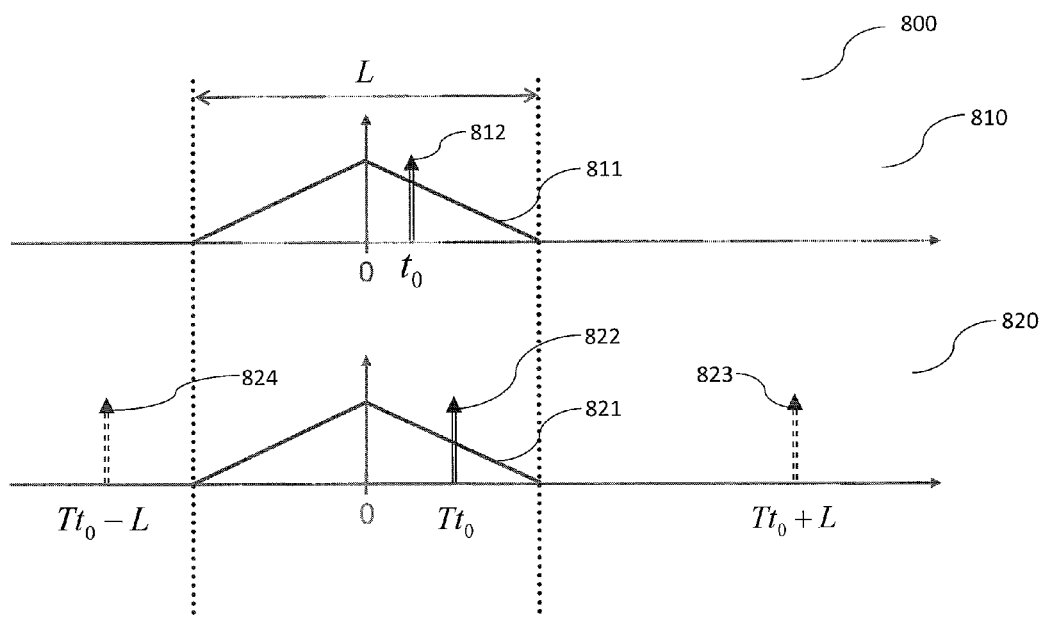
FIG. 8 illustrates a Dirac at a particular position as it appears in the analysis and synthesis windows of a harmonic transposer.

This is illustrated in FIG. 8 which shows the analysis and synthesis 800 of a Dirac pulse $\delta(t-t_0)$. The upper part of FIG. 8 shows the input to the analysis stage 810 and the lower part of FIG. 8 shows the output of the synthesis stage 820. The upper and lower graphs represent the time domain. The stylized analysis window 811 and synthesis window 821 are depicted as triangular (Bartlett) windows. The input pulse $\delta(t-t_0)$ 812 at time instant $t=t_0$ is depicted on the top graph 810 as a vertical arrow. It is assumed that the DFT transform block is of size $M=L=L_A=L_S$, i.e. the size of the DFT transform is chosen to be equal to the size of the windows. The phase multiplication of the subband signals by the factor T will produce the DFT analysis of a Dirac pulse $\delta(t-Tt_0)$ at $t=Tt_0$, however, of a Dirac pulse periodized to a Dirac pulse train with period L. This is due to the finite length of the applied window and Fourier Transform. The periodized pulse train with period L is depicted by the dashed arrows 823, 824 on the lower graph.

In a real-world system, the pulse train actually contains a few pulses only (depending on the transposition factor), one main pulse, i.e. the wanted term, a few pre-pulses and a few post-pulses, i.e. the unwanted terms. The pre- and post-pulses emerge because the DFT is periodic (with L). When a pulse is located within an analysis window, so that the complex phase gets wrapped when multiplied by T (i.e. the pulse is shifted outside the end of the window and wraps back to the beginning), an unwanted pulse emerges within the synthesis window. The unwanted pulses may have, or may not have, the same polarity as the input pulse, depending on the location in the analysis window and the transposition factor.

In the example of FIG. 8, the synthesis windowing uses a finite window $v_S$ 821. The finite synthesis window 821 picks the desired pulse $\delta(t-Tt_0)$ at $t=Tt_0$ which is depicted as a solid arrow 822 and cancels the other unwanted contributions which are shown as dashed arrows 823, 824.

As the analysis and synthesis stage move along the time axis according to the hop factor $\Delta s$ or the time stride $\Delta t$, the pulse $\delta(t-t_0)$ 812 will have another position relative to the center of the respective analysis window 811. As outlined above, the operation to achieve time-stretching consists in moving the pulse 812 to T times its position relative to the center of the window. As long as this position is within the window 821, this time-stretch operation guarantees that all contributions add up to a single time stretched synthesized pulse $\delta(t-Tt_0)$ at $t=Tt_0$.

Figure 9:
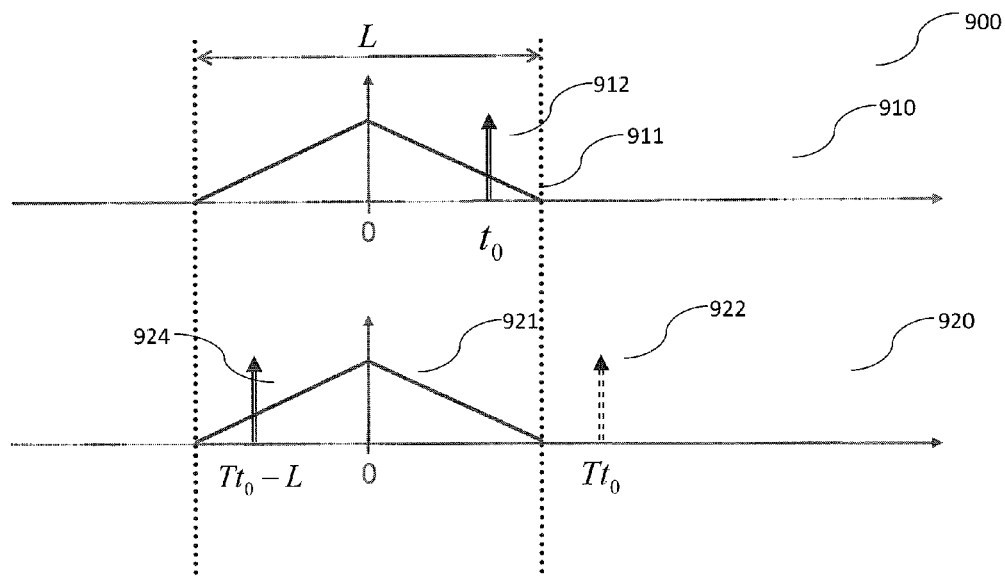
FIG. 9 illustrates a Dirac at a different position as it appears in the analysis and synthesis windows of a harmonic transposer.

However, a problem occurs for the situation of FIG. 9, where the pulse $\delta(t-t_0)$ 912 moves further out towards the edge of the DFT block. FIG. 9 illustrates a similar analysis/synthesis configuration 900 as FIG. 8. The upper graph 910 shows the input to the analysis stage and the analysis window 911, and the lower graph 920 illustrates the output of the synthesis stage and the synthesis window 921. When time-stretching the input Dirac pulse 912 by a factor T, the time stretched Dirac pulse 922, i.e. $\delta(t-Tt_0)$, comes to lie outside the synthesis window 921. At the same time, another Dirac pulse 924 of the pulse train, i.e. $\delta(t-Tt_0+L)$ at time instant $t=Tt_0-L$, is picked up by the synthesis window. In other words, the input Dirac pulse 912 is not delayed to a T times later time instant, but it is moved forward to a time instant that lies before the input Dirac pulse 912. The final effect on the audio signal is the occurrence of a pre-echo at a time distance of the scale of the rather long transposer windows, i.e. at a time instant $t=Tt_0-L$ which is $L-(T-1)t_0$ earlier than the input Dirac pulse 912.

Figure 10:
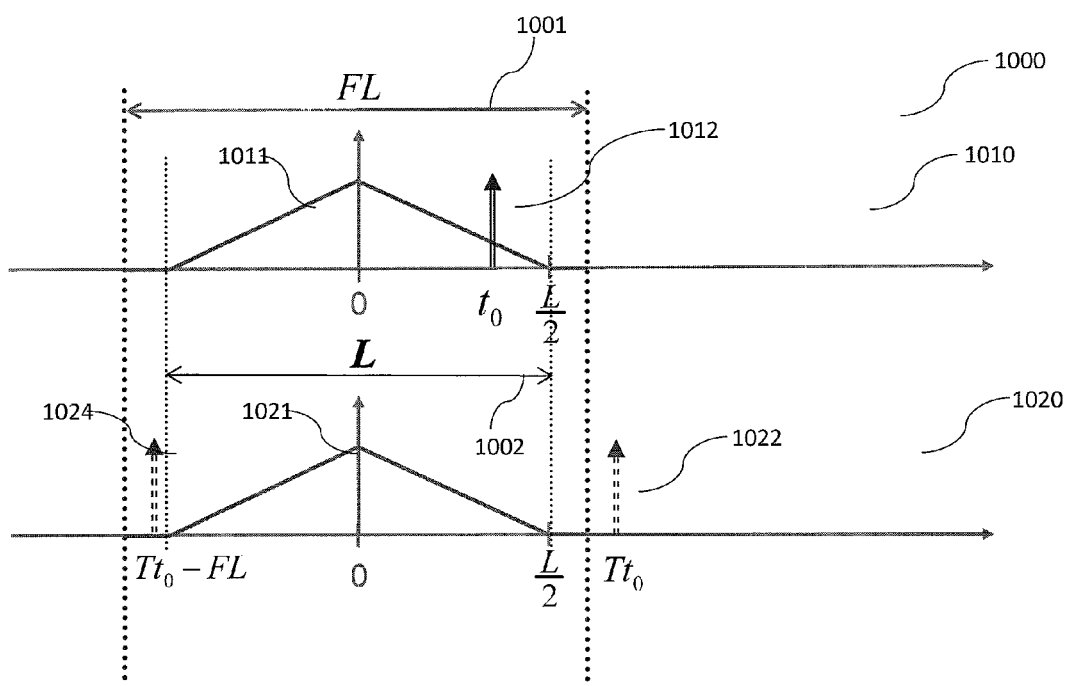
FIG. 10 illustrates a Dirac for the position of FIG. 9 as it will appear when using frequency domain oversampling.

The principle of the solution to this problem is described in reference to FIG. 10. FIG. 10 illustrates an analysis/synthesis scenario 1000 similar to FIG. 9. The upper graph 1010 shows the input to the analysis stage with the analysis window 1011, and the lower graph 1020 shows the output of the synthesis stage with the synthesis window 1021. The DFT size is adapted so as to avoid pre-echoes. This may be achieved by setting the size M of the DFT such that no unwanted Dirac pulse images from the resulting pulse train are picked up by the synthesis window. The size of the DFT transform 1001 is increased to M=FL, where L is the length of the window function 1002 and the factor F is a frequency domain oversampling factor. In other words, the size of the DFT transform 1001 is selected to be larger than the window size 1002. In particular, the size of the DFT transform 1001 may be selected to be larger than the window size 1002 of the synthesis window. Due to the increased length 1001 of the DFT transform, the period of the pulse train comprising the Dirac pulses 1022, 1024 is FL. By selecting a sufficiently large value of F, i.e. by selecting a sufficiently large frequency domain oversampling factor, undesired contributions to the pulse stretch can be cancelled. This is shown in FIG. 10, where the Dirac pulse 1024 at time instant $t=Tt_0-$FL lies outside the synthesis window 1021. Therefore, the Dirac pulse 1024 is not picked up by the synthesis window 1021 and by consequence, pre-echoes can be avoided.

It should be noted that in a preferred embodiment the synthesis window and the analysis window have equal "nominal" lengths (measured in the number of samples). However, when using implicit resampling of the output signal by discarding or inserting samples in the frequency bands of the transform or filter bank, the synthesis window size (measured in the number of samples) will typically be different from the analysis size, depending on the resampling and/or transposition factor.

The minimum value of F, i.e. the minimum frequency domain oversampling factor, can be deduced from FIG. 10. The condition for not picking up undesired Dirac pulse images may be formulated as follows: For any input pulse $\delta(t-t_0)$ at position $$t = t_0 < \frac{L}{2}, \text{ i.e.}$$

for any input pulse comprised within the analysis window 1011, the undesired image $\delta(t-Tt_0+FL)$ at time instant $t=Tt_0-FL$ must be located to the left of the left edge of the synthesis window at $$t = -\frac{L}{2}.$$

In an equivalent manner, the condition $$T\frac{L}{2} - FL \leq -\frac{L}{2}$$

must be met, which leads to the rule $$F \geq \frac{T+1}{2}. \tag{6}$$

As can be seen from formula (6), the minimum frequency domain oversampling factor F is a function of the transposition order T. More specifically, the minimum frequency domain oversampling factor F is proportional to the transposition order T.

By repeating the line of thinking above for the case where the analysis and synthesis windows have different lengths one obtains a more general formula. Let $L_A$ and $L_S$ be the lengths of the analysis and synthesis windows (measured in the number of samples), respectively, and let M be the DFT size employed. The general rule extending formula (6) is then $$M \geq \frac{TL_A + L_S}{2}. \tag{7}$$

That this rule indeed is an extension of (6) can be verified by inserting M=FL, and $L_A=L_S=L$ in (7) and dividing by L on both side of the resulting equation.

The above analysis is performed for a rather special model of a transient, i.e. a Dirac pulse. However, the reasoning can be extended to show that when using the above described time-stretching and/or harmonic transposition scheme, input signals which have a near flat spectral envelope and which vanish outside a time interval [a,b] will be stretched to output signals which are small outside the interval [Ta,Tb]. It can also be verified, by studying spectrograms of real audio and/or speech signals, that pre-echoes disappear in the stretched or transposed signals when the above described rule for selecting an appropriate frequency domain oversampling factor is respected. A more quantitative analysis also reveals that pre-echoes are still reduced when using frequency domain oversampling factors which are slightly inferior to the value imposed by the condition of formula (6) or (7). This is due to the fact that typical window functions $v_S$ are small near their edges, thereby attenuating undesired pre-echoes which are positioned near the edges of the window functions.

In summary, a way to improve the transient response of frequency domain harmonic transposers, or time-stretchers, has been described by introducing an oversampled transform, where the amount of oversampling is a function of the transposition factor chosen. The improved transient response of the transposer is obtained by means of frequency domain oversampling.

In the multiple transposer of FIG. 6, frequency domain oversampling may be implemented by using DFT kernels 601, 602, 603, 604 of length 1024F and by zero padding the analysis and synthesis windows symmetrically to that length. It should be noted that for complexity reasons, it is beneficial to keep the amount of oversampling low. If formula (6) is applied to the multiple transposer of FIG. 6, an oversampling factor F=2.5 should be applied to cover all the transposition factors T=2, 3, 4. However, it can be shown that the use of F=2.0 already leads to a significant quality improvement for real audio signals.

In the following, the use of frequency domain oversampling in the context of combined analysis/synthesis filter banks, such as described in the context of FIG. 5 or FIG. 6b, is described.

In general, for a combined transposition filter bank where the physical spacing $Q\Delta f$ of the synthesis filter bank subbands is Q times the physical spacing $\Delta f$ of the analysis filter bank and where the physical analysis window duration $D_A$ (measured in units of time, e.g. seconds) is also Q times that of the synthesis filter bank, $D_A = QD_S$, the analysis for a Dirac pulse as above will apply for all transposition factors T=Q, Q+1, Q+2, . . . as if T=Q. In other words, the rule for the degree of frequency domain oversampling required in a combined transposition filter bank is given by $$F \geq \frac{Q+1}{2}. \tag{6b}$$

In particular, it should be noted that for T>Q, the frequency domain oversampling factor $$F < \frac{T+1}{2}$$

is sufficient, while still ensuring the suppression of artifacts on transient signals caused by harmonic transposition of order T. I.e. using the above oversampling rules for the combined filter bank, it can be seen that even when using higher transposition orders T>Q, it is not required to further increase the oversampling factor F. As indicated by equation (6b), it is sufficient in the combined filter bank implementation of FIG. 6b to use an oversampling factor F=1.5 in order to avoid the occurrence of pre-echoes. This value is lower than the oversampling factor F=2.5 required for the multiple transposer of FIG. 6. Consequently, the complexity of performing frequency domain oversampling in order to improve the transient performance of multiple harmonic transposers can be further reduced when using a combined analysis/synthesis filter bank (instead of separate analysis and/or synthesis filter banks for the different transposition orders).

In a more general scenario, the physical time durations of the analysis and synthesis windows $D_A$ and $D_S$, respectively, may be arbitrarily selected. Then the physical spacing $\Delta f$ of the analysis filter bank subbands should satisfy $$\Delta f \leq \frac{2}{Q(D_A + D_S)}, \tag{7b}$$

in order to avoid the described artifacts caused by harmonic transposition. It should be noted that the duration of a window D typically differs from the length of a window L. Whereas the length of a window L corresponds to the number of signal samples covered by the window, the duration of the window D corresponds to the time interval of the signal covered by the window. As illustrated in FIG. 6a, the windows 611, 612, 613, 614 have an equal length of L=1024 samples. However, the duration $D_A$ of the analysis window 611 is T times the duration $D_S$ of the synthesis window 612, 613, 614, wherein T is the respective transposition order and the resolution factor of the respective synthesis filter bank. In a similar manner, the duration $D_A$ of the analysis window 611 in FIG. 6b is Q times the duration $D_S$ of the synthesis window 612, wherein Q is the resolution factor of the synthesis filter bank. The duration of a window D is related to the length of the window L via the sampling frequency $f_s$, i.e. notably $$D = \frac{L}{f_S}.$$

In a similar manner, the frequency resolution of a transform $\Delta f$ is related to the number of points or length M of the transform via the sampling frequency $f_s$, i.e. notably $$\Delta f = \frac{f_S}{M}.$$

Furthermore, the physical time stride $\Delta t$ of a filter bank is related to the hop size $\Delta s$ of the filter bank via the sampling frequency $f_s$, i.e. notably $$\Delta t = \frac{\Delta s}{f_S}.$$

Using the above relations, equation (6b) may be written as $$\Delta f D_A = Q \Delta f D_S \leq \frac{2}{Q+1}, \tag{6c}$$

i.e. the product of the frequency resolution and the window length of the analysis filter bank and/or the frequency resolution and the window length of the synthesis filter bank should be selected to be smaller or equal to $$\frac{2}{Q+1}.$$

For T>Q, the product $\Delta f D_A$ and/or $Q\Delta f D_S$ may be selected to be greater than $$\frac{2}{T+1},$$

thereby reducing the computational complexity of the filter banks.

In the present document, various methods for performing harmonic transposition of signals, preferably audio and/or speech signals, have been described. Particular emphasis has been put on the computational complexity of multiple harmonic transposers. In this context, a multiple transposer has been described, which is configured to perform multiple orders of transposition using a combined analysis/synthesis filter bank, i.e. a filter bank comprising a single analysis filter bank and a single synthesis filter bank. A multiple tranposer using a combined analysis/synthesis filter bank has reduced computational complexity compared to a conventional multiple transposer. Furthermore, frequency domain oversampling has been described in the context of combined analysis/synthesis filter banks. Frequency domain oversampling may be used to reduce or remove artifacts caused on transient signals by harmonic transposition. It has been shown that frequency domain oversampling can be implemented at reduced computational complexity within combined analysis/synthesis filter banks, compared to conventional multiple transposer implementations.

While specific embodiments of the present invention and applications of the invention have been described herein, it will be apparent to those of ordinary skill in the art that many variations on the embodiments and applications described herein are possible without departing from the scope of the invention described and claimed herein. It should be understood that while certain forms of the invention have been shown and described, the invention is not to be limited to the specific embodiments described and shown or the specific methods described.

The methods and systems described in the present document may be implemented as software, firmware and/or hardware. Certain components may e.g. be implemented as software running on a digital signal processor or microprocessor. Other components may e.g. be implemented as hardware and or as application specific integrated circuits. The signals encountered in the described methods and systems may be stored on media such as random access memory or optical storage media. They may be transferred via networks, such as radio networks, satellite networks, wireless networks or wireline networks, e.g. the internet. Typical devices making use of the methods described in the present document are for example media players or setup boxes which decode audio signals. On the encoding side, the systems and methods may be used e.g. in broadcasting stations and at multimedia production sites.

The invention claimed is:

1. A audio signal processing device for generating a high frequency component for an audio signal, the audio signal processing device comprising:
   an analysis window unit to apply an analysis window of a length of $L_A$ samples on the audio signal;
   an analysis transformation unit of order M and having a frequency resolution $\Delta f$, to transform the $L_A$ samples into M complex coefficients;
   a nonlinear processing unit to alter the phase of the complex coefficients by using a transposition order T;
   a synthesis transformation unit of order M and having a frequency resolution $Q\Delta f$, to transform the altered coefficients into time domain samples, wherein Q is a frequency resolution factor; and
   a synthesis window unit to apply a synthesis window of a length of $L_S$ samples to the time domain samples;
   wherein the transformation order M depends on the transposition order T, the analysis window size $L_A$ and the synthesis window size $L_S$.

2. The audio signal processing device of claim 1, wherein the transformation order M is $M=F \cdot L_S$ and wherein $$F \geq \frac{Q+1}{2}.$$

3. The audio signal processing device of claim 2, wherein $$F < \frac{T+1}{2}.$$

4. The audio signal processing device of claim 1, wherein the transformation order M satisfies:

$$M \geq \frac{QL_A + L_S}{2}.$$

5. The audio signal processing device of claim 1, wherein the analysis transformation unit performs one of a Fourier Transform, a Fast Fourier Transform, a Discrete Fourier Transform, a Wavelet Transform; and
   the synthesis transformation unit performs the corresponding inverse transform.

6. The audio signal processing device of claim 1, wherein the analysis and/or synthesis window is one of:
   Gaussian window;
   cosine window;
   Hamming window;
   Hann window;
   rectangular window;
   Bartlett window;
   Blackman window.

7. The audio signal processing device of claim 1 further comprising:
   a second nonlinear processing unit to alter the phase of the complex coefficients by using a second transposition order $T_2$; wherein the transposition order T and the second transposition order $T_2$ are different; and
   a combining unit configured to combine the complex coefficients altered by the transposition order T and the second transposition order $T_2$ as input to the synthesis transformation unit.

8. The audio signal processing device of claim 7, wherein the combining unit is configured to superpose complex coefficients altered by the transposition order T and the second transposition order $T_2$ corresponding to overlapping frequency ranges.

9. The audio signal processing device of claim 1, wherein a sampling rate of the audio signal is $f_A$;
the analysis window is shifted by an analysis hop size of $\Delta s_A$ samples along the audio signal;
the frequency resolution of the analysis transform unit is $$\Delta f = \frac{f_A}{M};$$

a duration of the analysis window is $$D_A = \frac{L_A}{f_A};$$

a physical time stride of the analysis window is $$\Delta t_A = \frac{\Delta s_A}{f_A}.$$

10. The audio signal processing device of claim 1, wherein
a sampling rate of the high frequency component is $f_S = Qf_A$;
the synthesis window is shifted by a synthesis hop size of as $\Delta s_S$ Samples Along the high frequency component;
the frequency resolution of the synthesis transformation unit is $$Q\Delta f = \frac{f_S}{M};$$

a duration of the synthesis window is $$D_S = \frac{L_S}{f_S};$$

and
a physical time stride of the synthesis window is $$\Delta t_S = \frac{\Delta s_S}{f_S} = \frac{\Delta s_A}{f_A} = \Delta t_A.$$

11. A method, performed by an audio processing device comprising one or more processors, for generating a high frequency component for an audio signal, the method comprising:
applying an analysis window of a length of $L_A$ samples on the audio signal;
transforming the $L_A$ samples into M complex coefficients using an analysis transformation of order M and frequency resolution $\Delta f$;
altering the phase of the complex coefficients by using a transposition order T;
transforming the altered coefficients into time domain samples using a synthesis transformation of order M and frequency resolution $Q\Delta f$, wherein Q is a frequency resolution factor; and
applying a synthesis window of a length of $L_s$ samples to the time domain samples;
wherein the transformation order M depends on the transposition order T, the analysis window size $L_A$ and the synthesis window size $L_S$; wherein one or more of applying an analysis window, transforming the $L_A$ samples, altering the phase of the complex coefficients, and applying a synthesis window is implemented, at least in part, by one or more hardware elements of the audio processing device.

12. The method of claim 11, wherein the transformation order M is $M = F \cdot L_S$ and wherein $$F \geq \frac{Q+1}{2}.$$

13. The method of claim 12, wherein $$F < \frac{T+1}{2}.$$

14. The method of claim 11, wherein the transformation order M satisfies:

$$M \geq \frac{QL_A + L_S}{2}.$$

15. The method of claim 11, wherein
the analysis transformation is one of a Fourier Transform, a Fast Fourier Transform, a Discrete Fourier Transform, a Wavelet Transform; and
the synthesis transformation is a corresponding inverse transform of the analysis transformation.

16. The method of claim 11, wherein the analysis and/or synthesis window is one of:
Gaussian window;
cosine window;
Hamming window;
Hann window;
rectangular window;
Bartlett window;
Blackman window.

17. The method of claim 11 further comprising:
altering the phase of the complex coefficients by using a second transposition order $T_2$; wherein the transposition order T and the second transposition order $T_2$ are different; and
combining the complex coefficients altered by the transposition order T and the second transposition order $T_2$ as input to the synthesis transformation.

18. The method of claim 11, wherein
a sampling rate of the audio signal is $f_A$;
the analysis window is shifted by an analysis hop size of $\Delta s_A$ samples along the audio signal;
the frequency resolution of the analysis transformation is $$\Delta f = \frac{f_A}{M};$$

a duration of the analysis window is $$D_A = \frac{L_A}{f_A};$$

a physical time stride of the analysis window is $$\Delta t_A = \frac{\Delta s_A}{f_A}.$$

19. The method of claim 11, wherein a sampling rate of the high frequency component is $f_S=Qf_A$;

the synthesis window is shifted by a synthesis hop size of as $\Delta s_S$ samples along the high frequency component;

the frequency resolution of the synthesis transformation unit is $$Q\Delta f = \frac{f_S}{M};$$

a duration of the synthesis window is $$D_S = \frac{L_S}{f_S};$$

and
a physical time stride of the synthesis window is $$\Delta t_S = \frac{\Delta s_S}{f_S} = \frac{\Delta s_A}{f_A} = \Delta t_A.$$

20. A non-transitory computer readable storage medium comprising instructions, wherein, when executed by an audio signal processing device comprising one or more processors, the instructions cause the audio signal processing device to perform a method for generating a high frequency component for an audio signal, the method comprising:

applying an analysis window of a length of $L_A$ samples on the audio signal;

transforming the $L_A$ samples into M complex coefficients using an analysis transformation of order M and frequency resolution $\Delta f$;

altering the phase of the complex coefficients by using a transposition order T;

transforming the altered coefficients into time domain samples using a synthesis transformation of order M and frequency resolution $Q\Delta f$, wherein Q is a frequency resolution factor; and applying a synthesis window of a length of $L_s$ samples to the time domain samples;

wherein the transformation order M depends on the transposition order T, the analysis window size $L_A$ and the synthesis window size $L_S$; wherein one or more of applying an analysis window, transforming the $L_A$ samples, altering the phase of the complex coefficients, and applying a synthesis window is implemented, at least in part, by one or more hardware elements of the audio processing device.

* * * * *